(12) United States Patent
Alevizache et al.

(10) Patent No.: US 9,993,447 B2
(45) Date of Patent: Jun. 12, 2018

(54) SYSTEMS AND METHODS FOR INCREASING AGMATINE CELLULAR UPTAKE BY ORAL ADMINISTRATION

(71) Applicant: JW Nutritional, LLC, Dallas, TX (US)

(72) Inventors: Dragos Alevizache, McKinney, TX (US); Jesse Windrix, Allen, TX (US)

(73) Assignee: JW Nutritional, LLC, Allen, TX (US)

( * ) Notice: Subject to any disclaimer, the term of this patent is extended or adjusted under 35 U.S.C. 154(b) by 12 days.

(21) Appl. No.: 15/263,879

(22) Filed: Sep. 13, 2016

(65) Prior Publication Data

US 2017/0071883 A1    Mar. 16, 2017

Related U.S. Application Data

(60) Provisional application No. 62/218,271, filed on Sep. 14, 2015.

(51) Int. Cl.
| | |
|---|---|
| *A61K 31/122* | (2006.01) |
| *A61K 31/155* | (2006.01) |
| *A61K 45/06* | (2006.01) |
| *C07C 277/08* | (2006.01) |

(52) U.S. Cl.
CPC .......... *A61K 31/155* (2013.01); *A61K 31/122* (2013.01); *A61K 45/06* (2013.01); *C07C 277/08* (2013.01)

(58) Field of Classification Search
CPC .................................................. A61K 31/122
See application file for complete search history.

(56) References Cited

U.S. PATENT DOCUMENTS

| | | | |
|---|---|---|---|
| 5,077,313 A * | 12/1991 | Lubec | ............... A61K 31/13 514/565 |
| 5,677,349 A | 10/1997 | Gilad et al. | |
| 7,816,407 B2 | 10/2010 | Crooks et al. | |
| 7,867,948 B2 | 1/2011 | Gastner et al. | |
| 8,466,187 B2 | 6/2013 | Kramer et al. | |
| 8,927,031 B2 | 1/2015 | Blotsky et al. | |
| 2002/0065323 A1* | 5/2002 | Crooks | ............. A61K 31/155 514/631 |
| 2005/0096369 A1 | 5/2005 | Hoang | |
| 2009/0286750 A1* | 11/2009 | Kasubick | ......... A61K 31/7004 514/23 |

(Continued)

OTHER PUBLICATIONS

Crea Tona (https://supplementreviews.com/redefine/crea-trona, accessed Sep. 30, 2017).*

*Primary Examiner* — Benjamin Packard
(74) *Attorney, Agent, or Firm* — Kirby B. Drake; Klemchuk LLP (57) ABSTRACT

Formulations of hydrosoluble stable organic salts including, but not limited to, agmatine orotate, agmatine di-hydrochloride, agmatine phosphate, buffered agmatine or spray dried buffered agmatine base, whether alone or in combination with one another, are provided, as well as methods for making same. These agmatine salts may have improved solubility in aqueous and organic media and may have increased absorbability and/or tissue bioavailability in humans and animals when compared to agmatine sulfate. These formulations may be administered as a means for improving athletic performance, training resistance and/or cognitive function. These formulations also may increase cellular uptake of agmatine in an animal or human.

18 Claims, 5 Drawing Sheets

(56) References Cited

U.S. PATENT DOCUMENTS

2013/0053393 A1* 2/2013 Frangakis ............ A61K 31/497
514/252.16
2015/0005387 A1 1/2015 Moulinoux
2015/0086523 A1 3/2015 Gilad et al.

* cited by examiner

SYSTEMS AND METHODS FOR INCREASING AGMATINE CELLULAR UPTAKE BY ORAL ADMINISTRATION

CROSS REFERENCE TO RELATED APPLICATION

The present patent application is a U.S. non-provisional patent application of, and claims the benefit under 35 U.S.C. § 120 to U.S. provisional patent application Ser. No. 62/218,271, filed Sep. 14, 2015, which is incorporated herein by reference.

FIELD OF THE DISCLOSURE

The present disclosure generally relates to agmatine formulations and methods of administration, and more particularly to agmatine salts having increased absorbability and/or tissue bioavailability.

BACKGROUND

Agmatine, also known as (4-aminobutyl)guanidine, is an aminoguanidine. It is a natural compound synthesized by decarboxylation of the amino acid, arginine, also known as decarboxylated arginine.

Prior studies, such as "Agmatine Is Efficiently Transported by Non-Neuronal Monoamine Transporters Extraneuronal Monoamine Transporter (EMT) and Organic Cation Transporter 2 (OCT2)," by Dirk Grundemann et al., Department of Pharmacology, University of Cologne, accepted Oct. 30, 2002, have demonstrated that agmatine can be efficiently transported by non-neuronal monoamine transporters, extraneuronal monoamine transporters (EMT) and organic cation transporters 2 (OCT2). However, these studies have focused almost exclusively on agmatine sulfate, which has not been shown to provide sufficiently desirable bioavailability.

SUMMARY

Embodiments of the present disclosure may provide new forms of agmatine that may be more bioavailable because they are administered with a buffered media, such as Effer-Soda® (sodium carbonate/bicarbonate). Using a buffered media, agmatine may not be protonated as quickly as when it is administered on its own or in an agmatine sulfate form. When an alkaline pH is employed, improved transport and cell absorption of agmatine has been observed. Various agmatine salts, including but not limited to, agmatine phosphate, agmatine orotate, and agmatine di-hydrochloride may be employed according to embodiments of the present disclosure. Each of these new forms of agmatine may have good solubility in water as well as good buffering capacity on their own. These new forms of agmatine also may exhibit better performance because it takes more effort to protonate the amine group within each of the above-identified agmatine salts, and this may result in an improved uptake rate of agmatine into cells, leading to better bioavailability.

Embodiments of the present disclosure may provide an agmatine salt formation comprising an agmatine salt; and a buffered media, wherein the agmatine salt is not protonated as quickly as when it is administered on its own or in an agmatine sulfate form. The agmatine salt may be selected from the group comprising: agmatine phosphate, agmatine orotate, and agmatine di-hydrochloride. The agmatine salt formulation may be administered to animals and humans as a means for improving athletic performance, training resistance and/or cognitive function. The effective amount of agmatine salt may range from approximately 1.00 mg/kg/day to approximately 150 mg/kg/day. The agmatine salt formulation may be provided as a nutritional supplement in one of the following forms: tablets, hard gelatin capsules, ready-to-drink powders, soft gels, chewable tablets, gummies, effervescent powders, effervescent tablets, and bars. The agmatine salt may comprise approximately 0.100 g to approximately 5.0 g of the agmatine salt formulation. The agmatine salt formulation may further comprise one or more of the following: minerals, mineral salts, vitamins, herbs, stimulants including caffeine, alpha yohimbine, yohimbine hydrochloride, and phenylethylamine, plasma expanders such as glycerol, organic or inorganic sources of nitrates such as beet root extract or sodium nitrate, coenzyme Q10, ATP, and ribose. The buffered media may be selected from the group comprising: Crea-Trona, arginine base, Effer-Soda, potassium carbonate, and potassium bicarbonate. The buffered media may be arginine base and the agmatine salt formulation may have a pH of greater than 8.

Other embodiments of the present disclosure may provide an agmatine salt formulation comprising: an agmatine salt; a buffered media; and one or more additional components, wherein the agmatine salt formulation may provide for increased cellular uptake of agmatine in animals or humans and may have increased absorbability and/or tissue bioavailability in humans and animals when compared to agmatine sulfate. The agmatine salt may be agmatine phosphate, the buffered media may be Crea-Trona and/or Effer Soda, and the one or more additional components may be comprised of D-ribose, ubiquinol, thiamine mononitrate, adenosine 5'-triphosphate disodium, and pyridoxal 5' phosphate. The agmatine salt may be agmatine phosphate, the buffered media may be arginine base and/or Crea-Trona, and the one or more additional components may be comprised of D-ribose, ubiquinol, thiamine mononitrate, adenosine 5'-triphosphate disodium, and pyridoxal 5' phosphate. The agmatine salt may be agmatine dihydrochloride, the buffered media may be Effer-Soda and/or Crea-Trona, and the one or more additional components may be comprised of D-ribose, ubiquinol, thiamine mononitrate, adenosine 5'-triphosphate disodium, and pyridoxal 5' phosphate. The agmatine salt may be agmatine dihydrochloride, the buffered media may be arginine base and/or Crea-Trona, and the one or more additional components may be comprised of D-ribose, ubiquinol, thiamine mononitrate, adenosine 5'-triphosphate disodium, and pyridoxal 5' phosphate. The agmatine salt may be agmatine orotate, the buffered media may be Effer-Soda and/or Crea-Trona, and the one or more additional components may be comprised of D-ribose, ubiquinol, thiamine mononitrate, adenosine 5'-triphosphate disodium, and pyridoxal 5' phosphate. The agmatine salt may be agmatine orotate, the buffered media may be arginine base and/or Crea-Trona, and the one or more additional components may be comprised of D-ribose, ubiquinol, thiamine mononitrate, adenosine 5'-triphosphate disodium, and pyridoxal 5' phosphate. The agmatine salt may be agmatine sulfate, the buffered media may be Effer-Soda and/or Crea-Trona, and the one or more additional components may be comprised of D-ribose, ubiquinol, thiamine mononitrate, adenosine 5'-triphosphate disodium, and pyridoxal 5' phosphate. The agmatine salt may be agmatine sulfate, the buffered media may be arginine base/or Crea-Trona, and the one or more additional components may be comprised of D-ribose, ubiquinol, thiamine mononitrate, adenosine 5'-triphosphate disodium, and pyridoxal 5' phosphate.

Further embodiments of the present disclosure may provide a method to produce an agmatine salt formulation resulting in increased agmatine cellular uptake, the method comprising introducing a buffer into an agmatine salt to form the agmatine salt formulation having a pH in the range of 7.5-9.0, wherein the concentration of the agmatine salt in the agmatine salt formulation may range from 10% to 95%. One of the following steps may be performed after introducing the buffer: concentrating the agmatine salt formulation and transferring to a spray drier; transforming the agmatine salt formulation into a spray dried powder; or granulating the agmatine salt formulation.

BRIEF DESCRIPTION OF THE DRAWINGS

For a more complete understanding of this disclosure, reference is now made to the following description, taken in conjunction with the accompanying drawings, in which.

DETAILED DESCRIPTION

Embodiments of the present disclosure may provide compositions and formulations comprising, consisting essentially of, or consisting of hydrosoluble stable organic salts including, but not limited to, agmatine orotate, agmatine di-hydrochloride, agmatine phosphate, buffered agmatine or spray dried buffered agmatine base, whether alone or in combination with one another, as well as methods for making said compositions and formulations. Agmatine salts, such as those identified above, may have improved solubility in aqueous and organic media when compared to agmatine sulfate. Agmatine salts according to embodiments of the present disclosure may have increased absorbability and/or tissue bioavailability in humans and animals when compared to agmatine sulfate.

Compounds and formulations according to embodiments of the present disclosure may be administered to animals and humans as a means for improving athletic performance, training resistance and/or cognitive function. An effective amount of an agmatine salt according to embodiments of the present disclosure may be administered, and this effective amount may range from approximately 1.00 mg/kg/day to approximately 150.00 mg/kg/day. In some embodiments of the present disclosure, the agmatine salt formulation may be provided as a nutritional supplement, and the agmatine salt may comprise approximately 0.100 g to about 5.0 g inclusive without departing from the present disclosure.

Figure 1:
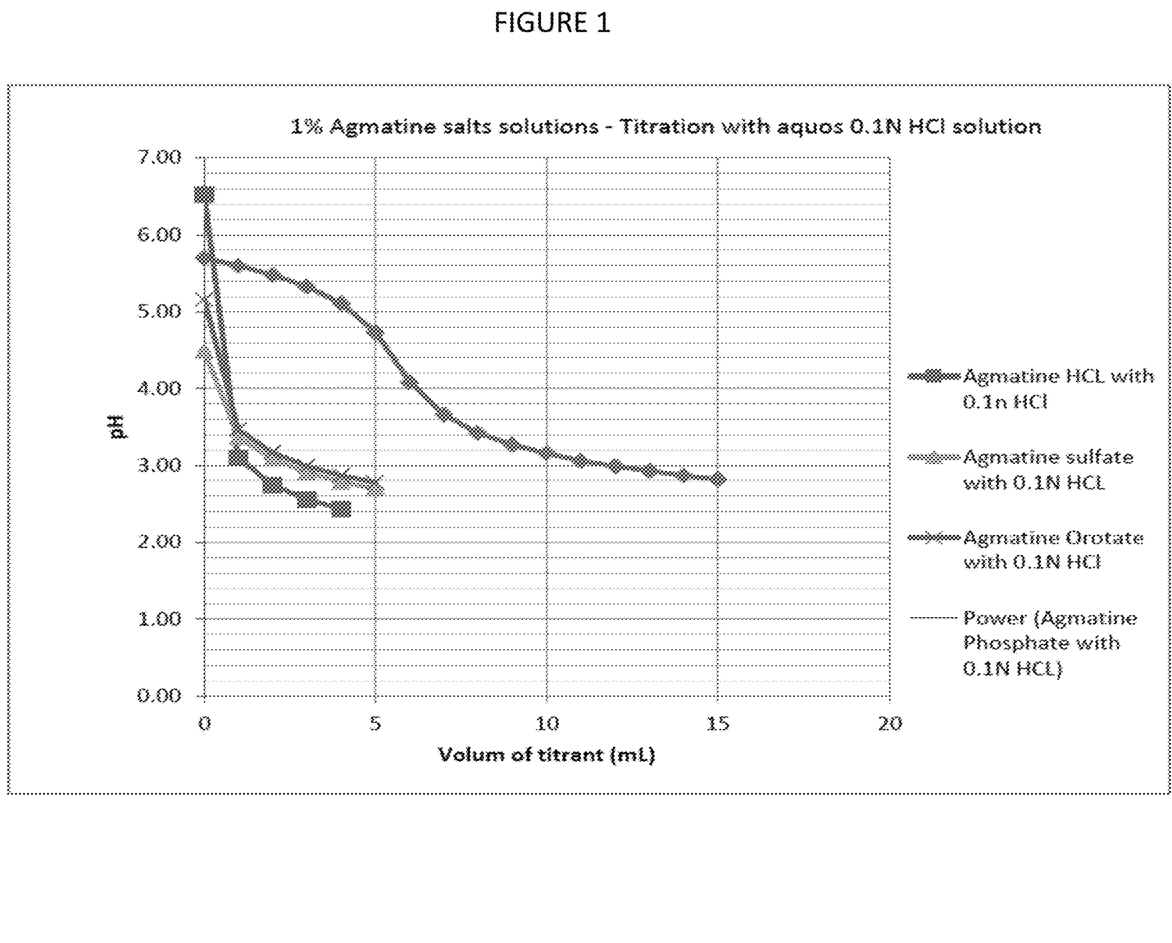
FIG. 1 depicts a graphical representation of 1% agmatine salt solutions in a titration with an aqueous 0.1N HCl solution according to an embodiment of the present disclosure.
Figure 2:
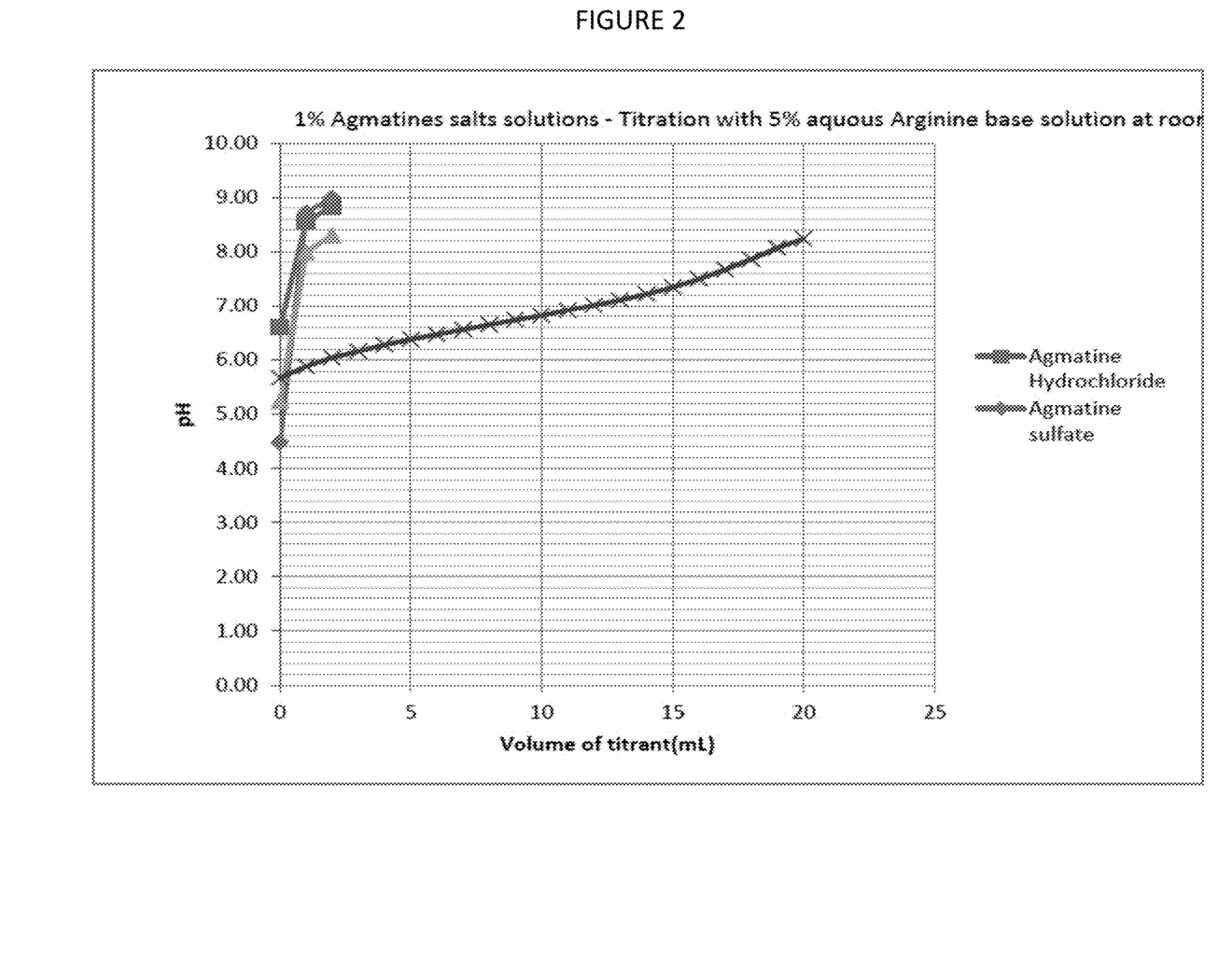
FIG. 2 depicts a graphical representation of 1% agmatine salt solutions in a titration with an 5% aqueous arginine base solution at room temperature according to an embodiment of the present disclosure.

Compounds and formulations according to embodiments of the present disclosure may provide a method to increase cellular uptake of agmatine in an animal or human. It should be appreciated that agmatine uptake may increase dramatically with increasing pH, and protonation of the amino group of agmatine is dependent on pH. The guanidinium group in agmatine has a pH of about 12.5 in aqueous solution while the amino group in agmatine has a pH of about 9. At the physiological pH, agmatine may be protonated and thus, requires transporters for uptake into the cells to occur. The fraction of the molecules having a single positive charge may increase as pH increases. Measuring pH of 1% agmatine salt solutions in purified water at room temperature for agmatine dihydrochloride, agmatine phosphate, and agmatine sulfate reveals that the most acidic is agmatine sulfate with a pH of 4.8 followed by agmatine phosphate with pH 5.7 and finally agmatine dihydrochloride at pH=6.4. This is reflected in FIGS. 1 and 2.

The pH dependence has been evaluated in acidic as well as basic conditions. Agmatine phosphate was shown to possess the capacity to act as a buffer when solutions of 1% concentration were titrated with 5% arginine base or 0.1N hydrochloric acid. About 15 mL of 0.1N HCl may be used to lower the pH of agmatine phosphate at around 3 while other agmatine salts, at the same concentration and in the same measuring conditions, required approximately 2-4 mL to change to an acidic pH. The same kind of behavior was observed when solutions of agmatine salts were titrated with a solution of agmatine base. About 20 mL were required to make the pH alkaline (above 8) in the case of agmatine phosphate, while other agmatine salts required approximately 2-3 mL to achieve the same pH range. Taking these observations into consideration along with the fact that better uptake of agmatine is observed at a higher pH, it should be appreciated that agmatine dihydrochloride and agmatine phosphate may be more desirable agmatine salts than agmatine sulfate for improving bioavailability of orally administered agmatine.

Formulations according to embodiments of the present disclosure may include agmatine salts and other amino acids, including but not limited to, citrulline, and they be formed alone or in combination with one or more minerals, mineral salts, vitamins, herbs and/or herbal extracts as shown in more detail below. Formulations according to embodiments of the present disclosure also may include stimulants including but not limited to caffeine, alpha yohimbine, yohimbine hydrochloride, and phenylethylamine, plasma expanders such as glycerol, organic or inorganic sources of nitrates such as beet root extract or sodium nitrate, coenzyme Q10, ATP, and/or ribose without departing from the present disclosure.

Certain components of formulations according to embodiments of the present disclosure may have a dietary intake purpose. Accordingly, a brief overview of certain components is provided below.

A primary component in formulations according to embodiments of the present disclosure is agmatine. Agmatine is naturally synthesized from arginine through arginine decarboxylation. Agmatine degradation occurs typically through hydrolysis, catalyzed by agmatinase into urea and putrescine. Agmatine has been detected in various human tissues such as the brain, lung, stomach, and spleen, and is typically present at concentrations less than approximately 100 mg/ml in human serum. Agmatine also exhibits diverse biological effects through imidazoline binding sites and α2-adrenergic receptors at much higher concentrations. While the function of agmatine at a physiological concentration may not be fully understood, agmatine exerts no cytotoxic effects at a concentration of 1 mM, while a lethal dose in a rat experimental model was 1-10 mg/kg. Agmatine has two functional groups: a guanadino group and a primary amino group. The pKa value of the guanadino group is 12.5, allowing for protonation, and thus, possession of a positive charge over a wide pH range. Moreover, the primary amino group has nucleophilicity and may be useful in coupling reactions.

D-ribose is a pentose monosaccharide that is produced in the human body where it then may bind to various nucleic acids. Such a binding process may allow these nucleic acids to act as energy intermediates, including, but not limited to, adenosine triphosphate (ATP), nicotinamide adenine dinucleotide (NADH), and flavin adenine dinucleotide (FADH). The binding process also may help to form the structural basis of DNA and RNA. During exercise, ATP is eventually degraded to inosine 5'-monophosphate (IMP) which does not serve an energy role and, if remaining in the cell, can be restored into ATP once a rest state is entered. Some IMP may then leave the cell in the forms of inosine or hypoxanthine, generally with higher intensities for longer periods, and in the context of heavy and frequent training, there may be overall purine loss. One study using high dose oral D-ribose supplementation "Effect of ribose supplementation on resynthesis of adenine nucleotides after intense intermittent training in humans," Am. J. Physiol. Regul. Integr. Comp. Physiol. 2004 January; 286(1):R182-8, has shown that the rate of ATP replenishment over three days of rest is greater with a surplus of D-ribose in the diet (approximately 150 g over the course of three days) when compared to a placebo sugar, such as maltodextrin.

Effer-Soda is a highly stable mixture of surface modified sodium carbonate and sodium bicarbonate powder. A study published in the Journal of the International Society of Sports Nutrition entitled "Sodium bicarbonate intake improves high-intensity intermittent exercise performance in trained young men" concluded that a high-intensity intermittent exercise performance is improved by prior intake of sodium bicarbonate in trained young men, with concomitant elevations in blood alkalosis and peak blood lactate levels, as well as lowered rating of perceived exertion.

Adenosine 5'-monophosphate disodium is another component of agmatine formulations according to some embodiments of the present disclosure. A study published in Nutrition and Metabolism by Wilson at al., concluded that oral supplementation with ATP in combination with high-intensity, periodized resistance training (RT), increases muscle mass, strength, and power compared with a placebo-matched control. Moreover, when faced with greater training frequencies, oral ATP may prevent typical declines in performance that are characteristic of overreaching. Future research may elucidate the underlying mechanisms through which ATP operates to promote improvements in training adaptations.

Crea-Trona® is also known as buffered creatine. During the fabrication process, AlzChem uses a double buffer from sodium carbonate and sodium bi-carbonate, both natural minerals, which creates an alkaline environment with a pH value between 8 and 12. Crea-Trona is more efficient than other types of creatine, including those with an alkaline pH-buffer (kre-alkalynes). The double buffer prevents the pH-value in the muscles from dropping rapidly during the workout. This may lead to a larger training volume and may stimulate faster recovery of the original pH-value after the workout.

Coenzyme Q10 (CoQ10) is a fat-soluble nutrient produced naturally by the human body. It may be concentrated in organs that require the most energy, such as the heart, liver, muscles and kidneys, as it is important in the process of producing cellular energy. In the body, CoQ10 may exist in an oxidized form (ubiquinone) or in a reduced unoxidized form (ubiquinol). When ubiquinone is used by the body, it becomes ubiquinol, and ubiquinol becomes ubiquinone when it carries out its role in the body. CoQ10 may play various roles in energy production with respect to cells in muscles. Factors that can negatively influence CoQ10 levels may include declining concentration of the coenzyme in the tissue due to different pathological changes, as well as intensive training and aging. Long lasting and intensive efforts through sports training likewise can contribute to this reduction of CoQ10 levels. Studies have shown that CoQ10 can mitigate muscle damage after high level training. CoQ10 was previously considered to be an ineffective substance for athletes, as past studies with CoQ10 did not give consistent results, but this may be due to study design or by delivery of an insufficient CoQ10 dosage. A study "Ubiquinol supplementation enhances peak power production in trained athletes: a double-blind, placebo controlled study", Alf et al., showed that "daily supplementation of 300 mg Ubiquinol for 6 weeks significantly enhanced physical performance measured as maximum power output by +0.08 W/kg bw (+2.5%) versus a placebo in young healthy trained German Olympic athletes. While adherence to a training regimen itself resulted in an improvement in peak power output, as observed by improvement in the placebo group, the effect of Ubiquinol supplementation significantly enhanced peak power production in comparison to placebo."

Pyridoxal 5' phosphate (the active form of vitamin B6) may be another component of agmatine formulations according to embodiments of the present disclosure. A study published by the American Society for Clinical Nutrition, "Effect of physical activity on thiamine, riboflavin, and vitamin B-6 requirements," shows that exercise appears to decrease nutrient status even further in active individuals with preexisting marginal vitamin intakes or marginal body stores. Thus, active individuals who restrict their energy intake or make poor dietary choices are at greatest risk for poor thiamine, riboflavin, and vitamin B6 status.

Thiamine mononitrate is a stable nitrate salt form of thiamine (vitamin B1). It has been shown to improve vasodilation (the widening of blood vessels) in patients with high blood sugar levels or diabetes. This response was not seen in patients with normal blood sugar levels. Therefore, inclusion of thiamine mononitrate may increase the effects of vasodilators in these patients. Using thiamine mononitrate in formulations according to embodiments of the present disclosure is not only to provide thiamine benefits but also for the vasodilatation purpose of nitric oxide supplementation from the nitrate content of thiamine mononitrate.

Several formulations are contemplated according to embodiments of the present disclosure. While these formulations are described below, it should be appreciated that other formulations may be provided without departing from the present disclosure. It also should be appreciated that different amounts of each component of the formulations may be included without departing from the present disclosure.

A first formulation according to an embodiment of the present disclosure may include approximately 1000 mg agmatine phosphate, approximately 500 mg D-ribose, approximately 300 mg ubiquinol, approximately 250 mg thiamine mononitrate, approximately 500 mg adenosine 5'-triphosphate disodium, approximately 25 mg pyridoxal 5' phosphate, and approximately 1500 mg Crea-Trona.

A second formulation according to an embodiment of the present disclosure may include approximately 1000 mg agmatine phosphate, approximately 500 mg Effer-Soda, approximately 500 mg D-ribose, approximately 300 mg ubiquinol, approximately 250 mg thiamine mononitrate, approximately 500 mg adenosine 5'-triphosphate disodium, approximately 25 mg pyridoxal 5' phosphate, and approximately 1500 mg Crea-Trona.

A third formulation according to an embodiment of the present disclosure may include approximately 1000 mg agmatine phosphate, approximately 500 mg arginine base, approximately 500 mg D-ribose, approximately 300 mg ubiquinol, approximately 250 mg thiamine mononitrate, approximately 500 mg adenosine 5'-triphosphate disodium, approximately 25 mg pyridoxal 5' phosphate, and approximately 1500 mg Crea-Trona.

A fourth formulation according to an embodiment of the present disclosure may include approximately 1000 mg agmatine dihydrochloride, approximately 500 mg Effer-Soda, approximately 500 mg D-ribose, approximately 300 mg ubiquinol, approximately 250 mg thiamine mononitrate, approximately 500 mg adenosine 5'-triphosphate disodium, approximately 25 mg pyridoxal 5' phosphate, and approximately 1500 mg Crea-Trona.

A fifth formulation according to an embodiment of the present disclosure may include approximately 1000 mg agmatine dihydrochloride, approximately 500 mg arginine base, approximately 500 mg D-ribose, approximately 300 mg ubiquinol, approximately 250 mg thiamine mononitrate, approximately 500 mg adenosine 5'-triphosphate disodium, approximately 25 mg pyridoxal 5' phosphate, and approximately 1500 mg Crea-Trona.

A sixth formulation according to an embodiment of the present disclosure may include approximately 1000 mg agmatine orotate, approximately 500 mg Effer-Soda, approximately 500 mg D-ribose, approximately 300 mg ubiquinol, approximately 250 mg thiamine mononitrate, approximately 500 mg adenosine 5'-triphosphate disodium, approximately 25 mg pyridoxal 5' phosphate, and approximately 1500 mg Crea-Trona.

A seventh formulation according to an embodiment of the present disclosure may include approximately 1000 mg agmatine orotate, approximately 500 mg arginine, approximately 500 mg D-ribose, approximately 300 mg ubiquinol, approximately 250 mg thiamine mononitrate, approximately 500 mg adenosine 5'-triphosphate disodium, approximately 25 mg pyridoxal 5' phosphate, and approximately 1500 mg Crea-Trona.

An eighth formulation according to an embodiment of the present disclosure may include approximately 1000 mg agmatine sulfate, approximately 500 mg Effer-Soda, approximately 500 mg D-ribose, approximately 300 mg ubiquinol, approximately 250 mg thiamine mononitrate, approximately 500 mg adenosine 5'-triphosphate disodium, approximately 25 mg pyridoxal 5' phosphate, and approximately 1500 mg Crea-Trona.

A ninth formulation according to an embodiment of the present disclosure may include approximately 1000 mg agmatine sulfate, approximately 500 mg arginine, approximately 500 mg D-ribose, approximately 300 mg ubiquinol, approximately 250 mg thiamine mononitrate, approximately 500 mg adenosine 5'-triphosphate disodium, approximately 25 mg pyridoxal 5' phosphate, and approximately 1500 mg Crea-Trona.

The above-referenced formulations were used to study the capacity of different agmatine salts in combination with different buffer media in order to evaluate the increased population of mono-protonated species of agmatine present, thereby increasing the concentration of the substrate of the species that may be transported into the cells through non-neuronal monoamine transporters, EMT and OCT2.

To maximize the benefits of oral administration of agmatine salts according to embodiments of the present disclosure, a buffer media may be used in formulations, or a stable mono-protonated or neutral form of such agmatine salts should be administered instead. As reflected in the formulations described above according to embodiments of the present disclosure, different buffer media have been used including Crea-Trona (such as that offered by AlzChem), arginine base, as well as Effer-Soda (such as that offered by SPI Pharma). However, it should be appreciated that other buffer media, such as potassium carbonate or potassium bicarbonate, may be utilized without departing from the present disclosure. Such buffer media may elevate the pH of the formulation. It also should be appreciated that different ratios of buffers may be utilized without departing from the present disclosure. As reflected in the above-referenced formulations, arginine base may be utilized according to some embodiments of the present disclosure. Arginine base in solution may have a basic pH (around 10) at room temperature and may act as a strong buffer system. When arginine base is combined with an agmatine salt in different ratios according to embodiments of the present disclosure, a solution with a high basic pH (>8) may result. Co-administering agmatine with arginine base may also improve the bioavailability of agmatine according to embodiments of the present disclosure.

It should be appreciated that these formulations according to embodiments of the present disclosure may take different forms when produced, including, but not limited to, tablets, hard gelatin capsules as well as ready-to-drink powders, soft gels, chewable tablets, gummies, effervescent powders/tablets, and bars.

Figure 3:
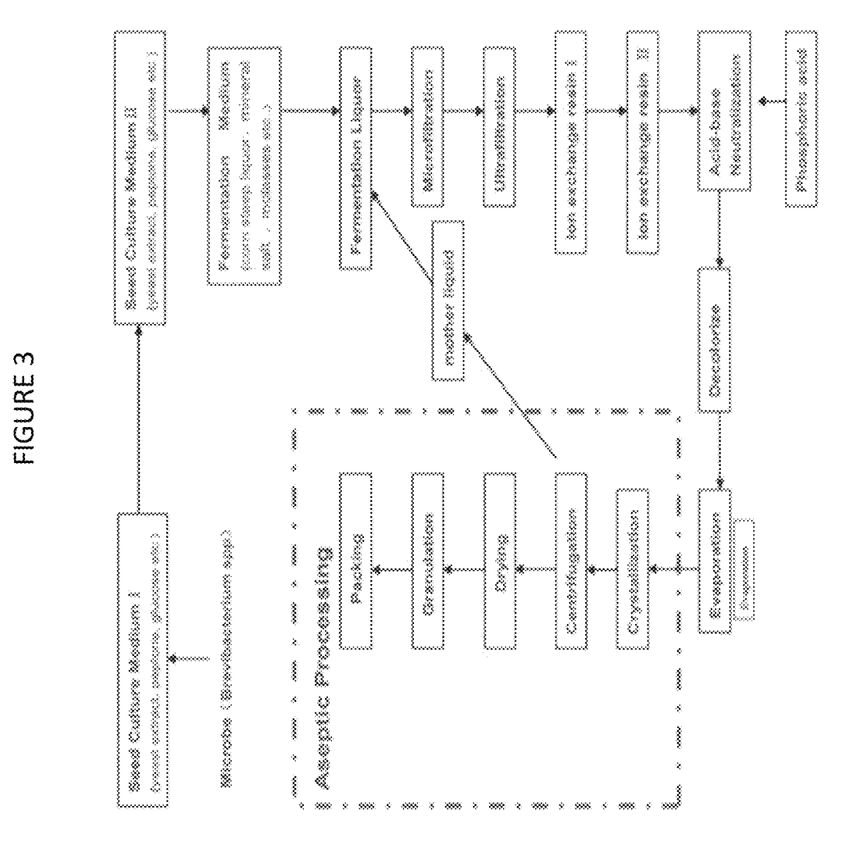
FIG. 3 depicts a flow chart for a method of preparation of agmatine phosphate according to an embodiment of the present disclosure.
Figure 4:
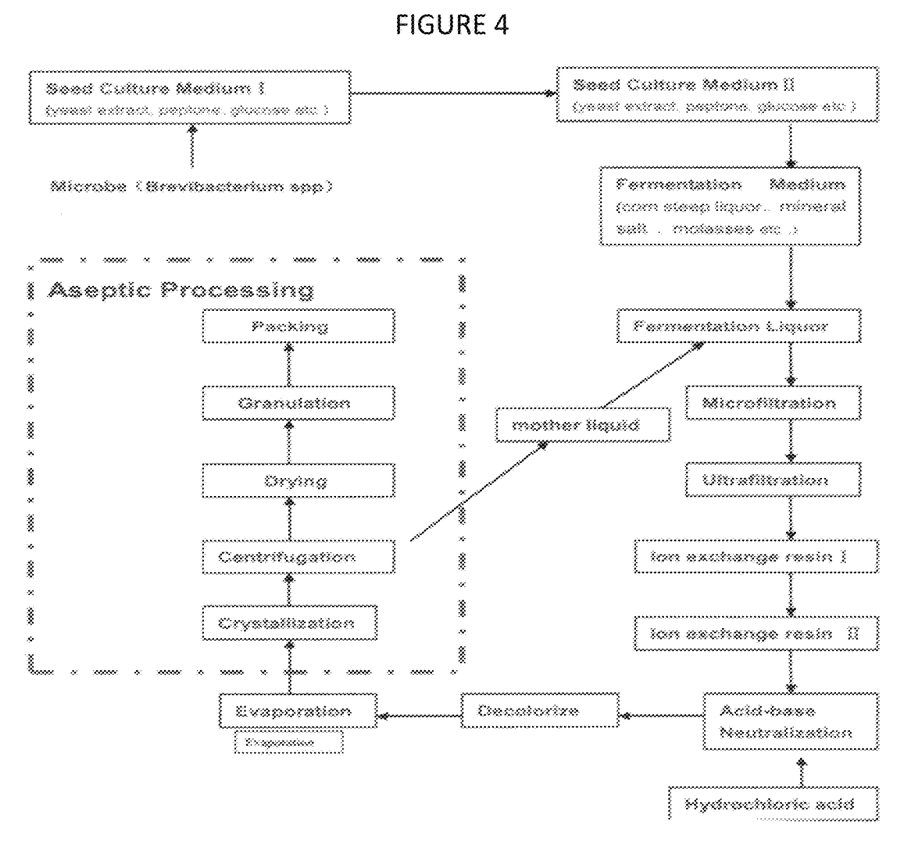
FIG. 4 depicts a flow chart for a method of preparation of agmatine hydrochloride according to an embodiment of the present disclosure.

Buffered agmatine salts according to embodiments of the present disclosure may be formed through a methodology similar to that depicted in FIGS. 3 and 4. While different steps are set forth in FIGS. 3 and 4, it should be appreciated that more or fewer steps may be utilized without departing from the present disclosure. It also should be appreciated that the steps may be performed in a different order without departing from the present disclosure.

FIG. 3 provides a flow chart of a method for producing agmatine phosphate according to an embodiment of the present disclosure. As shown in FIG. 3, starting with a microbe (*Brevibacterium* spp), a seed culture medium I (yeast extract, peptone, glucose, etc.) may be formed, and there may be a seed culture medium II (also yeast extract, peptone, glucose, etc.) formed from seed culture medium I. From seed culture medium II, a fermentation medium may be provided, including but not limited to, corn steep liquor, mineral salt, and/or molasses. A fermentation liquor may then be formed using the fermentation medium, and then various steps including microfiltration, ultrafiltration, ion exchange resin (one or more, depicted in FIG. 3 as ion exchange resin I and II), and acid-base neutralization may be performed. At the acid-base neutralization step, phosphoric acid may be introduced. Following acid-base neutralization, decolorization and evaporation may occur, and then aseptic processing may take place. Aseptic processing may include the following steps: crystallization, centrifugation, drying, granulation and packing. It should be appreciated that following the centrifugation step, further filtration may be needed, and in such instances, the mother liquid from the centrifugation process may be taken through the microfiltration, ultrafiltration, ion exchange resin, acid-base neutralization, decolorization and evaporation steps to be placed through aseptic processing again.

FIG. 4 provides a flow chart of a method for producing agmatine hydrochloride according to an embodiment of the present disclosure. As shown in FIG. 4, agmatine hydrochloride is formed through a process similar to that described in FIG. 3 for the formation of agmatine phosphate; however, at the acid-base neutralization step, hydrochloric acid is introduced rather than phosphoric acid.

Embodiments of the present disclosure also may provide methods to obtain a spray-dried agmatine base or buffered agmatine. Referring back to FIGS. 3 and 4, after the ion exchange resin II step forming the agmatine base, instead of proceeding to the neutralization step, a buffer may be introduced to make the resultant solution have a slightly basic pH, preferably in the range of 7.5-9.0, and more preferably around 8.0-9.0 but not to exceed a pH of 9.0 according to embodiments of the present disclosure. Following introduction of the buffer, the solution may be concentration and transferred to a spray drier to obtain the buffered agmatine. Alternatively, the solution may be transformed into a spray dried powder on a carrier selected from the group including, but not limited, to starch, food starch modified, calcium phosphate or mannitol. The concentration of agmatine in the resultant sprayed-dried agmatine base or buffered agmatine may vary from 10% to 95% depending on the application and/or requirements. The granulation can also be controlled by milling or sifting procedures.

A buffered, extended release form of agmatine salt may be produced by wet granulation or spray drying process using Carbopol 1 971P NF type of products and a mixture of agmatine salts/arginine base. Formulations with 3%-7% w/w carbopol 971P NF polymer have been shown to provide extended-release properties for up to approximately 12 hours. The ability of the polymer to extend the release at these low levels can be explained by its chemically cross-linked nature.

Structural characterization of the most stable geometries of agmatine at physiological condition is essential for understanding of its diverse biological role, namely its effect on mitochondrial permeability transition and its specific transport mechanism. It has been demonstrated in prior research (Structural Chemistry 2006, Antonio Toninello et al.) that the transport velocity is direct proportional to the concentration of the monopositive form of the molecule, the uptake increase drastically with increasing pH (6.5-9.0).

Figure 5:
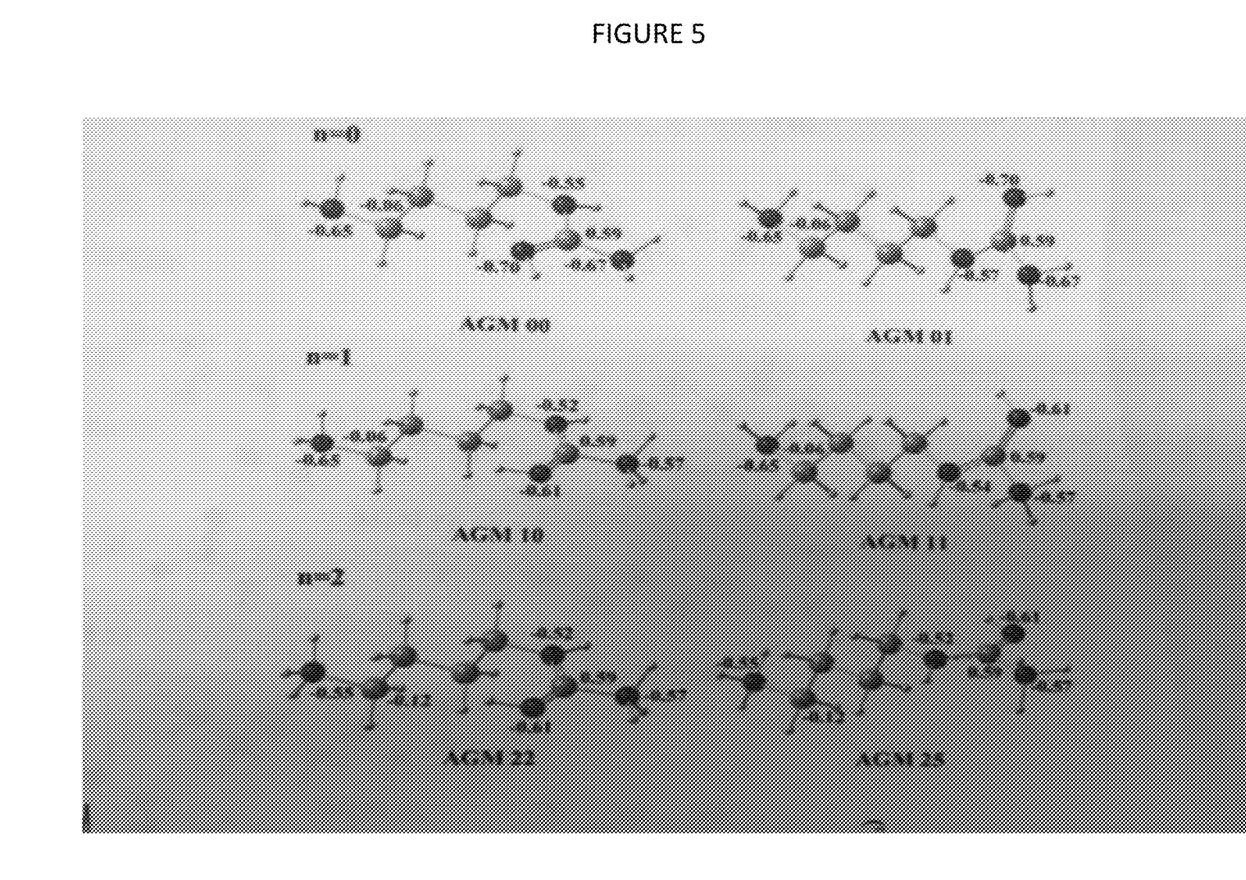
FIG. 5 depicts special Raman confrontational geometry of AGM 00, 01, 10, 11, 22 and 25 according to an embodiment of the present disclosure.

FIG. 5 depicts special Raman confrontational geometry of AGM 00, 01, 10, 11, 22 and 25 according to embodiments of the present disclosure. The predominant species at physiological pH=7.3 in aqueous solution will be di-cationic forms AGM 22 and AGM 25, displaying a lower negative charge in the protonated aliphatic amino terminal. At alkaline pH (7.3-9.0) the mono-protonated (monopositive) species AGM 10 and AGM 11 will be the most present, and at the very alkaline medium, the totally un-protonated (neutral) molecule—AGM 00 and AGM 01 will predominate.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. An agmatine salt formulation for oral administration as a nutritional supplement comprising:
   an agmatine salt; and
   arginine base,
   wherein the agmatine salt is not protonated as quickly as when it is administered on its own or in an agmatine sulfate form, and
   wherein the agmatine salt formulation has a pH of greater than 8.

2. The agmatine salt formulation of claim 1, wherein the agmatine salt is selected from the group comprising:
   agmatine phosphate, agmatine orotate, and agmatine di-hydrochloride.

3. The agmatine salt formulation of claim 1 wherein the agmatine salt formulation improves athletic performance, training resistance and/or cognitive function.

4. The agmatine salt formulation of claim 1 wherein the effective amount of agmatine salt ranges from approximately 1.00 mg/kg/day to approximately 150 mg/kg/day.

5. The agmatine salt formulation of claim 1 provided in one of the following forms:
   tablets, hard gelatin capsules, ready-to-drink powders, soft gels, chewable tablets, gummies, effervescent powders, effervescent tablets, and bars.

6. The agmatine salt formulation of claim 5 wherein the agmatine salt comprises approximately 0.100 g to approximately 5.0 g of the agmatine salt formulation.

7. The agmatine salt formulation of claim 1 further comprising one or more of the following:
   minerals, mineral salts, vitamins, herbs, stimulants, caffeine, alpha yohimbine, yohimbine hydrochloride, and phenylethylamine, plasma expanders, glycerol, organic or inorganic sources of nitrates, beet root extract, sodium nitrate, coenzyme Q10, ATP, and ribose.

8. An agmatine salt formulation for oral administration as a nutritional supplement comprising:
   an agmatine salt selected from the group comprising agmatine phosphate, agmatine orotate, and agmatine di-hydrochloride;
   a buffered media introduced into the agmatine salt; and
   D-ribose, ubiquinol, thiamine mononitrate, adenosine 5'-triphosphate disodium, and pyridoxal 5' phosphate,
   wherein the agmatine salt formulation provides for increased cellular uptake of agmatine in animals or humans and has increased absorbability and/or tissue bioavailability in humans and animals when compared to agmatine sulfate.

9. The agmatine salt formulation of claim 8 wherein the agmatine salt is agmatine phosphate, and the buffered media is double buffered creatine and/or sodium carbonate.

10. The agmatine salt formulation of claim 8 wherein the agmatine salt is agmatine phosphate, and the buffered media is arginine base and/or double buffered creatine.

11. The agmatine salt formulation of claim 8 wherein the agmatine salt is agmatine dihydrochloride, and the buffered media is sodium carbonate and/or double buffered creatine.

12. The agmatine salt formulation of claim 8 wherein the agmatine salt is agmatine dihydrochloride, and the buffered media is arginine base and/or double buffered creatine.

13. The agmatine salt formulation of claim 8 wherein the agmatine salt is agmatine orotate, and the buffered media is sodium carbonate and/or double buffered creatine.

14. The agmatine salt formulation of claim 8 wherein the agmatine salt is agmatine orotate, and the buffered media is arginine base and/or double buffered creatine.

15. The agmatine salt formulation of claim 8 wherein the agmatine salt is agmatine sulfate, and the buffered media is sodium carbonate and/or double buffered creatine.

16. The agmatine salt formulation of claim 8 wherein the agmatine salt is agmatine sulfate, and the buffered media is arginine base and/or double buffered creatine.

17. A method to produce an agmatine salt nutritional supplement resulting in increased agmatine cellular uptake upon oral administration, the method comprising:
    introducing a buffer into an agmatine salt to form the agmatine salt nutritional supplement having a pH in the range of 7.5-9.0,
    wherein the concentration of the agmatine salt in the agmatine salt nutritional supplement ranges from 10% to 95%.

18. The method of claim 17 wherein one of the following steps is performed after introducing the buffer:
    concentrating the agmatine salt nutritional supplement formulation and transferring to a spray drier;
    transforming the agmatine salt nutritional supplement into a spray dried powder; or
    granulating the agmatine salt nutritional supplement.

* * * * *